United States Patent
Ke et al.

(10) Patent No.: US 7,456,972 B2
(45) Date of Patent: Nov. 25, 2008

(54) SURFACE PLASMON INDUCTION IN MULTIWALLED CARBON NANOTUBE ARRAYS

(75) Inventors: Pu-Chun Ke, Clemson, SC (US); Francesco Stellacci, Somerville, MA (US); Apparao M. Rao, Anderson, SC (US)

(73) Assignee: Clemson University, Clemson, SC (US)

( * ) Notice: Subject to any disclaimer, the term of this patent is extended or adjusted under 35 U.S.C. 154(b) by 413 days.

(21) Appl. No.: 11/332,840

(22) Filed: Jan. 13, 2006

(65) Prior Publication Data

US 2008/0088845 A1    Apr. 17, 2008

Related U.S. Application Data

(60) Provisional application No. 60/643,573, filed on Jan. 13, 2005.

(51) Int. Cl.
*G01N 21/55* (2006.01)
(52) U.S. Cl. ............................ 356/445; 356/448
(58) Field of Classification Search ......... 356/445–448, 356/311, 317, 417
See application file for complete search history.

(56) References Cited

U.S. PATENT DOCUMENTS

| 6,040,936 | A | 3/2000 | Kim et al. |
|---|---|---|---|
| 6,287,765 | B1 | 9/2001 | Cubicciotti |
| 2004/0240157 | A1 | 12/2004 | Legagneux et al. |
| 2005/0175507 | A1* | 8/2005 | Tsukruk ............ 422/68.1 |
| 2005/0275934 | A1 | 12/2005 | Ballato et al. |
| 2006/0034729 | A1* | 2/2006 | Poponin ............ 422/82.05 |

OTHER PUBLICATIONS

Abstract of Article—*Elementary excitations in cylindrical tubules*, Lin et al., Phys. Rev. B 47, 1993, pp. 6617-6624.

Article—*Coupling of photon energy via a multiwalled carbon nanotube array*, Lu et al., Applied Physics Letters, vol. 87, 2005, pp. 173102-1 through 173102.3.

Article—*Nanotubes facilities surface plasmon resonance*, Lynn M. Savage, Biophotonics International, Photonoic Solutions for Biotechnology and Medicine, "Seeing More with Confocal Microscopy", Dec. 2005, p. 50.

Article—*Observation of Hybridization and Dehybridization of Thiol-Tethered DNA Using Two-Color Surface Plasmon Resonance Spectroscopy*, Peterlinz et al., J. Am. Chem. Soc., vol. 119, 1997, pp. 3401-3402.

Article—*Plasmon-coupled tip-enhanced near-field optical microscopy*, Bouhelier et al., Journal of Microscopy, vol. 210, Jun. 3, 2003, pp. 220-224.

Article—*Uniform patterned growth of carbon nanotubes without surface carbon*, Teo et al., Applied Physics Letters, vol. 79, No. 10, Sep. 3, 2001, pp. 1534-1536.

* cited by examiner

*Primary Examiner*—Gregory J Toatley, Jr.
*Assistant Examiner*—Tri T Ton
(74) *Attorney, Agent, or Firm*—Dority & Manning, PA

(57) ABSTRACT

Disclosed are optical devices including one or more carbon nanotubes that can function as plasmon waveguides. The presently disclosed devices advantageously utilize the existence of surface plasmons on carbon nanotubes through the generation and transport of surface plasmon polaritons across the nanotubes. Also disclosed are methods for tuning the devices through particular formation parameters for the nanotubes and/or selection of particular substrate materials. Systems of the present invention can provide optical data concerning a sample, for instance via construction of an NSOM image, as well as topological date concerning a sample via construction of an AFM image. In one embodiment, the disclosed systems can provide simultaneous acquisition of optical images and topological images.

28 Claims, 3 Drawing Sheets

SURFACE PLASMON INDUCTION IN MULTIWALLED CARBON NANOTUBE ARRAYS

CROSS REFERENCE TO RELATED APPLICATION

This application claims benefit of U.S. Provisional Application having Ser. No. 60/643,573 filed Jan. 13, 2005.

FEDERALLY SPONSORED RESEARCH AND DEVELOPMENT

The United States Government may have rights in this invention pursuant to National Science Foundation Grant No. NIRT 0210559.

BACKGROUND OF THE INVENTION

Over the last century, mankind has developed a growing understanding of the nature of light. This growing understanding has led to an increasing ability to harness and control light, which has in turn led to improvements in a wide variety of different technologies. For instance, the ability to control photons has led to improvements in communications, such as through the development of fiber optics; improvements in opto-electronics, such as through the development of photovoltaic cells; as well as the development of near-field optics, a field of study dedicated to the utilization of near-field light, which is the light created around the periphery of an object emitting or being illuminated by light. The study of near-field light has brought about the development of and continuing improvements to many optical devices including many different types of imaging devices as well as optical scanners, filters, switches, modulators, and the like.

Surface plasmon polaritons (also referred to throughout this disclosure as simply plasmons or SPP) exist when light couples with surface plasmons, which are collective electronic excitations running as longitudinal density fluctuations at the interface of a metal (or metallic material) with an adjacent dielectric material. The SPPs thus created can propagate across the metallic material and their energy can then be utilized, for instance via reradiation of the impinged light. Surface plasmons have been generated to advantage on metallic thin films having thickness on the order of tens of nanometers as well as on metallic nanoparticles and metallic nanoshells.

Utilization of plasmons has been seen in many varied applications including label-free monitoring of biomolecular interactions, enhanced DNA hybridization, single-molecule fluorescence imaging, two-photon excitation, molecular sensing, photonic transportation, and high-density nanolithography. For example, SPPs have proven quite useful in sensing technologies such as near-field scanning optical microscopy (NSOM). Traditional NSOM methods couple evanescent photons reflected, fluoresced, or otherwise contacted with a sample with surface plasmons generated on the tip of a near-field probe via location of the probe tip within the penetration depth of the evanescent waves (e.g., about 100 nm). This coupling can enhance and convert the evanescent photons to propagating photons that can then be collected and imaged using far-field optics.

Problems exist with known devices and methods, however. For example, the metallic thin films, nanoparticles, nanoshells, etc. used to generate the plasmon propagation can be difficult and expensive to prepare, but due to the internal damping effect common to such materials and subsequent energy attenuation with increased thickness, materials of such dimensions have been considered to be required in order to attain plasmon propagation. Other problems exist with these materials as well. For instance, heat generated at the metal can cause problems during use, including damage or destruction of samples being examined. In addition, and in particular during NSOM processes, the close proximity between the probe tip and the sample that is necessary to ensure photon-plasmon coupling can create shadow effects that can then detrimentally effect the imaging of the sample.

What is needed in the art are additional materials that can support surface plasmons to generate SPPs and methods for developing such materials to form optical devices.

SUMMARY OF THE INVENTION

In one embodiment, the present invention is directed to optical devices that include at least one carbon nanotube located on a substrate such that photons can couple with surface plasmons on the nanotube to give rise to surface plasmon polaritons. Either a single carbon nanotube can be used or a plurality of carbon nanotubes in an array can be used. Moreover, the nanotubes can be single-walled or multiwalled, as desired. The devices of the invention can also include a detector for detecting photonic energy radiated from the surface plasmon polaritons. Detectors encompassed by the invention include position point detectors, light intensity detectors, and the like.

The optical devices can also include a sample support. The sample support can be, for instance, the upper surface of an array of carbon nanotubes or can be a separate material, as desired.

During use of the device, a light source can provide photons that can couple with the surface plasmons at a first end of the carbon nanotube. The photonic energy can then be reradiated from a second end of the nanotube following plasmon transport across the nanotube. Accordingly, the device can function in one embodiment as a plasmon waveguide. The photonic energy radiated from the surface plasmon polaritons can contact a sample located on the sample support and the sample can be examined and/or imaged via the detected evanescent field following contact with the sample. Thus, the device can additionally function as an imaging device.

Optionally, the substrate can include a nonlinear optical material, for instance a nonlinear optical material that has a selectively variable index of refraction, and the optical characteristics of the device can be specifically tuned. The optical characteristics of the device can also be tuned through inclusion of a dopant in the carbon nanotube(s).

In one preferred embodiment, the devices of the present invention can include both a light intensity detector and a position sensing point detector. In this embodiment, both optical information and topological information about a sample can obtained, and, if desired, can be simultaneously obtained. The data obtained by the detectors can then be mapped to provide images of a sample. For instance both an NSOM image and an AFM image can be obtained.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying figures, in which.

Figure 1:
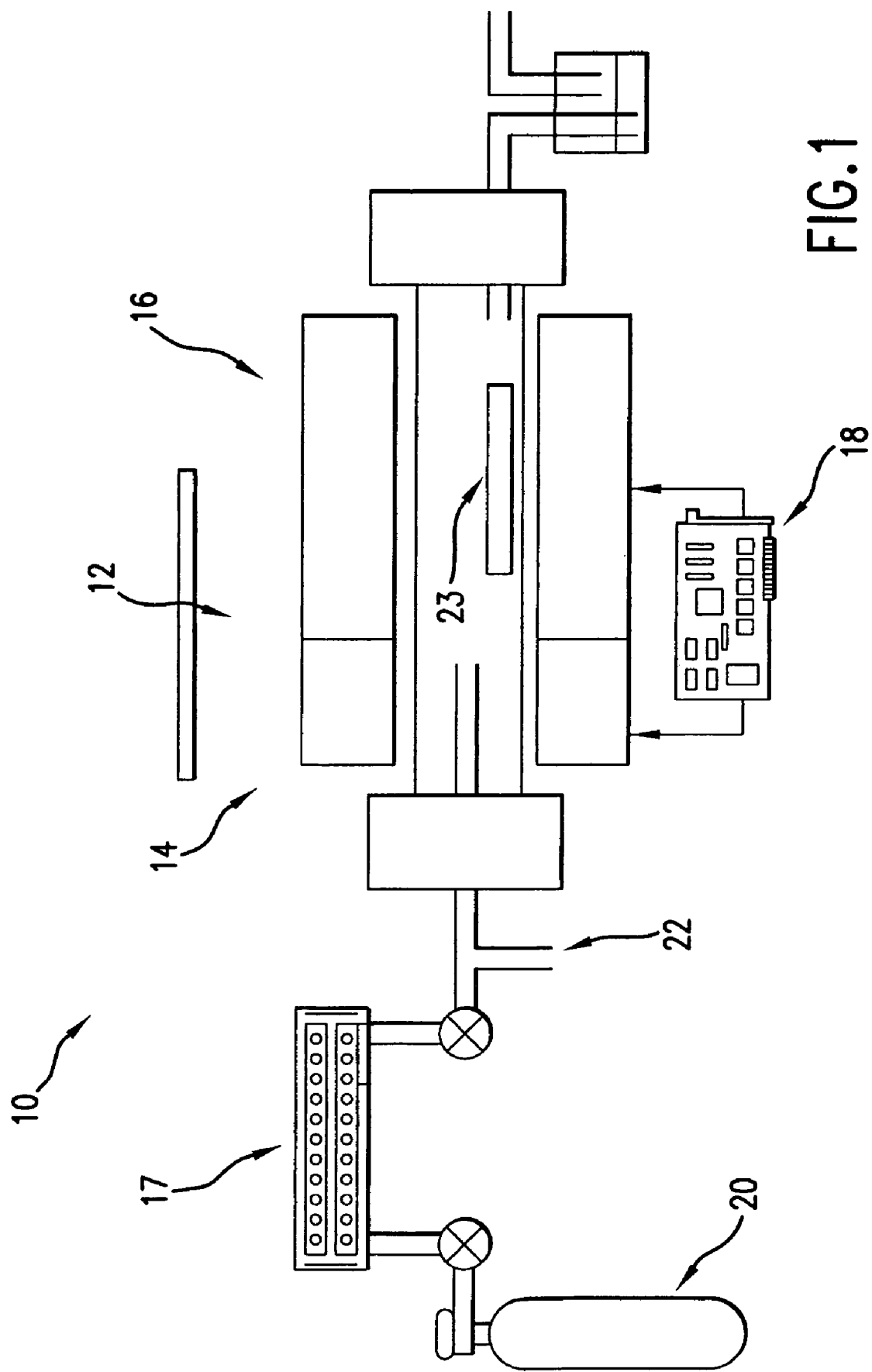
FIG. 1 is a schematic representation of one process for forming a MWNT array as may be used in the systems of the present invention.

Repeat use of reference characters in the present specification and drawings is intended to represent the same or analogous features or elements of the present invention.

DETAILED DESCRIPTION OF THE INVENTION

Reference will now be made in detail to various embodiments of the invention, one or more examples of which are illustrated in the accompanying Figures. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

In general, the present invention is directed to the recognition of the existence of surface plasmons on carbon-based nanotubes, and, in one embodiment, on multi-walled carbon nanotubes (MWNTs). More specifically, the invention is directed to methods, devices, and systems that advantageously utilize this previously unrecognized characteristic of nanotubes through the generation and transport of SPP's across the nanotubes.

Theoretically, individual multi-walled nanotubes have been suggested as a feasible source for generating plasmons. In particular, the framework of intra-subband and inter-subband plasmons has been developed in individual tubes as well as in two-dimensional (2D) arrays. To date, however, the bulk and surface plasmons in MWNTs have mainly been studied using electron energy loss spectroscopy (EELS) and the energy loss peaks have been attributed to $\pi$ and $\pi+\sigma$ plasmon excitations.

In accord with the present invention, disclosed are optical devices including one or more nanotubes that can be utilized as, for example, a tunable plasmon waveguide. The disclosed devices can beneficially be utilized for imaging illumination as well as biological and nano-optoelectronic sensing applications. For example, the disclosed devices can be utilized in imaging and sensing applications including near-field optical scanning microscopy (NSOM) as well as atomic force microscopy (AFM). In one particular embodiment, the devices and systems of the present invention can provide both the optical sensing capabilities of NSOM and the topological sensing capabilities of AFM to provide both optical and topological information about a sample of interest via a single system.

In one embodiment, the disclosed devices and systems can utilize carbon nanotubes according to methods similar to those in which metallic thin films and nanoparticles have been utilized in optical devices in the past. In contrast with such previously known devices, however, the nanotubes and systems of the present invention can be quickly, easily, and economically prepared. Moreover, the nanotubes of the disclosed devices can be utilized to efficiently transport photonic energy over much greater distances than the metallic films and particles utilized in the past. For example, MWNT arrays of the present invention can have a thickness on the order of two orders of magnitude greater than the thickness of the metallic thin films found in previously known optical devices.

While not wishing to be bound by any particular theory, the ability of nanotubes to efficiently propagate plasmons is understood to be attributed to the unique combination of the physical and the electrical characteristics of the nanotubes. For instance, every MWNT will have a high aspect ratio tubular metallic nanostructure and the electrons can flow on the outermost tube shells of the MWNT. Moreover, though each nanotube may be considered to be a quasi-two dimensional structure, it will have only a one dimensional electronic structure, stemming from a combination of the nanoscale tube diameter and the electronic structure of the graphite-derived material. This 1D electronic structure can allow each individual MWNT within the array to act as an electron carrier, i.e., a plasmon waveguide. Moreover, since the length of the individual MWNTs can be much less than the mean free path, which can be greater than 30 µm for MWNTs, ballistic transport may also contribute to SPP propagation across the array. As a result, the thickness of a MWNT layer in the disclosed devices can be much greater than that of the metallic thin film layers of previously known devices and still exhibit excellent photonic energy transportation characteristics.

Devices and systems of the present invention include one or more carbon-based nanotubes. For example, in one embodiment, a layer including a highly ordered array of multi-walled nanotubes can be utilized in which the plurality of individual MWNTs forming the array can be generally parallel to one another and perpendicular to a substrate to upon which the nanotubes are grown or otherwise applied. It should be understood, however, that the invention is not limited to this particular embodiment, and in other embodiments a single MWNT as well as less ordered arrays of MWNTs, e.g., nanotube mats, can be utilized. Moreover, the present invention is not limited to MWNTs, and in other embodiments, an individual or a plurality of single-walled nanotubes (SWNTs) in either an ordered array or a SWNT mat can be utilized in the disclosed systems.

In general, the method utilized to form the nanotubes is not critical to the invention. For example, in one embodiment, a highly ordered array of MWNTs can be formed on a substrate according to a chemical vapor deposition method, such as that illustrated in FIG. 1 at 10. System 10 can be used to grow highly aligned and high purity nanotubes according to a CVD process. For instance, system 10 can include a two-stage furnace 12 that can be controlled such as by temperature controller 18 to provide a preheater 14 and a reactor 16 within the furnace 12. Other standard process control measures and devices as are generally known in the art, such as mass flow controller 17, for example, can be included with the system 10 to control the process either manually or automatically.

An inert gas flow can be supplied to the system 10, such as via tank 20, to provide a carrier flow for materials into the furnace 12. System 10 can also include a port 22 for inserting reactants to system. For example, a carbon source such as xylene can be fed into the furnace 12 via injection port 22. The reactants can vaporize upon reaching the end of the pre-heater 14 (maintained at e.g., about 200° C.), and the vapors can then be carried into the reactor 16. A catalyst, such as iron for example, can be provided either on the surface of the substrate or in combination with the reactant flow, as is generally known in the art. For instance, in those embodiments in which a limited number of nanotubes is desired or a nanotube array is desired at a particular location on a substrate, catalyst can be deposited on the substrate in the desired amounts and/or locations prior to the deposition process.

The reactor 16 can be maintained at a temperature (e.g., between about 650° C. and about 750° C.) that can enable the reactants to decompose and form the MWNTs in a highly ordered array on the substrate 23.

It should be understood that the specific method of forming the nanotubes of the disclosed optical devices and/or locating the nanotubes on a substrate is not critical to the invention, and the described methods are merely exemplary, and not meant to be limiting in any way to the invention. For example, in one embodiment, a single nanotube can be located in a desired location on a substrate. According to this particular embodiment, a single nanotube can be formed in the desired location on the substrate or optionally can be formed in a separate process, as in a nanotube mat, and then isolated and located at the desired location on the substrate.

Various processes for locating very few or even a single nanotube are known to those of skill in the art. For example, one exemplary process, described by Legagneux, et al. (U.S. Patent Application Publication 2004/0240157) incorporated herein by referenced and also described by Teo, et al. (App. Phys. Lett. 79:10, 1534-1536) includes utilization of a catalyst and diffusion barrier thin films that are deposited onto substrates and lithographically patterned using a lift-off process. Diffusion barrier materials can include, for instance, $SiO_2$ and TiN. Upon annealing to the growth temperature, the thin film breaks up into nanoparticles which then seed the growth of the nanotubes. After reaching a reaction temperature (e.g., about 700° C.), the nanotube growth can be initiated by introducing $NH_3$ and $C_2H_2$ into the chamber and initiating a direct current (dc) glow dicharge. The nanotubes grown according to this method can be grown in a vacuum chamber, for instance at a base pressure of $10^{-2}$ Torr. Additional experimental details and growth characteristics are presented in the published U.S. Patent Application referenced above.

In general, individual MWNTs utilized in the disclosed optical devices can include at least two nested tubes and can be up to about 100 nanometers in total outer diameter. For example, in one embodiment, the individual MWNTs can be between about 10 and about 50 nm in outer diameter, or about 25 nm in outer diameter, in one particular embodiment. In addition, the individual MWNTs can be up to about 30 μm in length. For example, the individual nanotubes can be between about 1 μm and about 100 μm in length.

According to one embodiment of the invention, individual MWNTs can include a dopant. For example, MWNTs can be formed according to a CVD method, such as those described above, and a dopant can be included in the vapor fed to the reactor furnace. According to this embodiment, and depending upon particular formation parameters, such as, reaction conditions as well as dopant concentration, a percentage of the MWNTs forming an array can form with the inclusion of a dopant in the MWNT wall.

The addition of a dopant to individual MWNTs in an array can vary the electron carrying capacity of the array and consequently, the plasmon frequency of the device. In other words, the coupling frequency of the device can be shifted through the addition of one or more dopants to the array. Thus, in this particular embodiment, the device can be tuned so as to excite resonant coupling between the surface plasmons and the incoming light at a particular frequency. Possible dopants can generally include any element that can exchange charge with a carbon atom. For example, a non-limiting list of exemplary materials can include, without limitation, alkali metals, alkaline earth metals, halogens, boron, and nitrogen.

The devices of the present invention can include a substrate that can support the nanotubes. In general, any substrate that can allow the coupling of a light wave with the surface plasmons on the nanotubes can be utilized in the presently disclosed optical devices. For example, in one embodiment, the substrate can be merely a transparent dielectric material, such as an optical grade polymer, glass, or quartz, for example. In other embodiments, the substrate upon which the MWNTs can be located can be varied to provide particular characteristics to the optical devices of the present invention. For example, in one embodiment, the substrate of the optical device can include a nonlinear optical material having a selectively variable index of refraction. According to this embodiment, the characteristics of the substrate can be utilized to provide 'tunability' to the devices. For instance, the characteristics of the substrate can be utilized to shift the nature of the incoming light to the plasmon frequency of the nanotubes and encourage resonant coupling of the light with the surface plasmons.

In one embodiment, the substrate can include an electro-optic material that can exhibit a variable index of refraction that can be controlled through application of energy, such as through application of an electric field across the device. Exemplary electro-optic materials can include, without limitation, a liquid crystal material, a ferro-electric liquid crystal, a semiconductor layer or a polymer electro-optic film, such as those disclosed by Kim. et al. in U.S. Pat. No. 6,040,936, which is incorporated herein by reference as to all relevant material.

In another embodiment, the substrate can be a non-linear material that can exhibit a variable refractive index depending upon a characteristic of the incident light, including materials disclosed in co-owned U.S. patent application publication 2005/0275934 to Ballato, et al., which is incorporated herein as to all relevant material. Suitable substrates in this particular embodiment can include, but are not limited to, arsenic, sulfur, selenium, or germanium-containing chalcogenide glasses; silicon, germanium, or lead-containing oxide glasses; silicon, germanium, zinc, sulfur, selenium, cadmium, lead, or tellurium-containing semiconducting crystals; or nonlinear chromophore-containing polymers.

In yet another embodiment, the MWNT layer of the present invention can be utilized in conjunction with previously known optical devices. For example, in one embodiment, the substrate can be a metallic thin film, such as those utilized in previously known plasmon waveguide applications. According to this embodiment, a MWNT array of the present invention can be utilized to extend the distance of photonic energy transportation of these previously known devices to much greater distances than thought possible in the past.

The devices of the disclosed invention can optionally include additional layers and materials, as well. For example, additional layers can be included on either side of the devices that can, for instance, sandwich the substrate layer between the MWNT array and an additional layer or optionally sandwich the MWNT array between the substrate layer and an additional layer. In one embodiment, the device can be a multi-layer device with additional layers on both sides of the substrate/MWNT array composite. Additional layers can be any suitable material. For example, in one embodiment, an additional layer can include a material having a variable index of refraction including, for instance, a variable index of refraction depending upon a characteristic of the incident light, or an electro-optic material, in which the index of refraction can vary with regard to an electric field established across the material.

Figure 2:
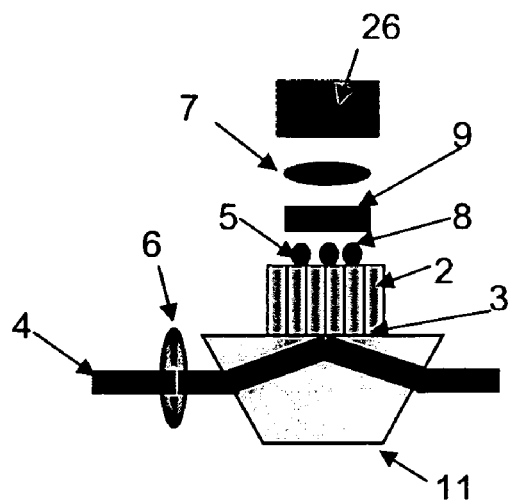
FIG. 2 is a schematic representation of one system of the present invention.

One embodiment of an optical system of the present invention is schematically illustrated in FIG. 2. This particular system can be utilized in one particular embodiment in an optical imaging process such as, for instance, an NSOM process.

According to this embodiment, the system includes an array of highly aligned nanotubes 2. The array 2 can be located directly on a prism 11 or optionally on a substrate (not shown) that can in turn be location on a prism 11. Any device as is known in the art can optionally be used to control the incident light to the substrate. For instance, the array 2 can be grown on a substrate, as discussed above, and the substrate including array 2 thereon can be mounted on prism 11 via immersion in oil for index matching. According to this embodiment, the 1/2 interface 5 at the surface of array 2 with air (or any other medium) can be utilized as a stage for a sample 8 that can be examined and optionally imaged by the system. For example, an optical imaging system including a long working distance lens 7 and a light intensity detector 26, optionally with an emission filter 9, can be used. Any suitable light intensity detector can be used with the disclosed systems including, but not limited to, spectrometers, photo diodes (e.g., avalanche photo diodes), photomultiplier tubes, charge-coupled devices (CCD), and the like.

During use, light 4 can be incident at the prism/air interface under the condition of total internal reflection such that evanescent waves are generated at the 0/1 interface 3 between the base of the nanotubes and the prism or substrate. Optionally, the nature of the incident light can be controlled. For instance, a half waveplate 6 can be utilized to control the polarization of the incident light and ensure coupling of the incident photons with the surface plasmons on the nanotubes. The plasmons can then reradiate photons and generate an enhanced evanescent field at the 1/2 interface 5. The enhanced field can be utilized in examination of the sample. For example, in this particular embodiment, including light intensity detector 26, the enhanced evanescent field can be utilized to construct an optical image of the sample, for instance through mapping the data according to known NSOM imaging techniques.

Data obtained at the light intensity detector 26 can be utilized to form an image according to any mechanism as is known in the art including, without limitation, polarization, topography, birefringence, index of refraction, fluorescence, wavelength dependence, reflectivity, and the like.

Figure 3:
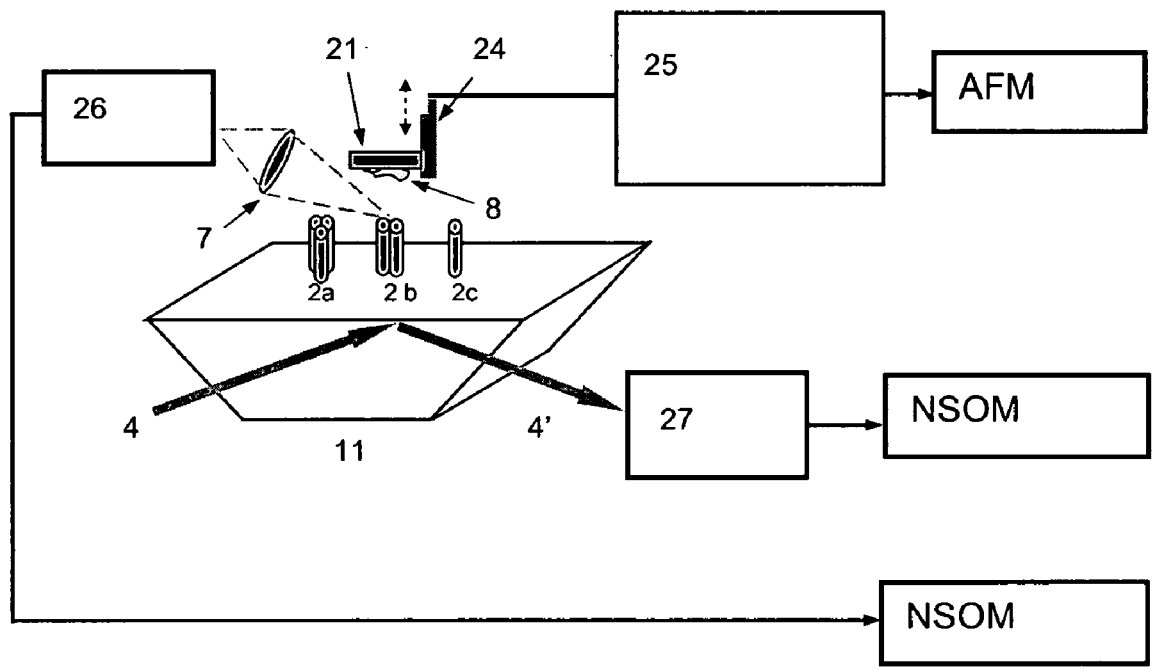
FIG. 3 is a schematic representation of another system of the present invention.

Another embodiment of a system according to the present invention is schematically illustrated in FIG. 3. According to this embodiment, a system can provide both the optical sensing capabilities of NSOM and the topological sensing capabilities of AFM, and in one embodiment, can do so simultaneously.

As can be seen with reference to the figure, in this particular embodiment the sample 8 can be mounted on a sample holder 21 that is capable of motion in response to the atomic forces existing between the sample 8 and the nanotube(s) 2. For example, sample holder 21 can be a portion of or in mechanical communication with a position sensing point detector 24 as shown. Any suitable position sensing point detector 24 can be utilized including, for example, a tuning fork, a cantilever, or any other position sensing point detector capable of detecting deflection of the sample holder 21 upon the interaction of the sample 8 with the evanescent field generated from the plasmons on the nanotubes 2. Position sensing point detector 24 can utilize any suitable methodology to detect the deflection. For example, the deflection can be measured through utilization of piezoresistive probes with force feed back loop for distance control as is generally known in the art. Any alternative method can be utilized as well. For instance, according to another embodiment, deflection can be measured using a laser spot reflected from a spot of the position sensing point detector 24 and into an array of photodiodes.

If desired, the sample holder 21 can be moveable so as to position the sample 8 in three dimensions with respect to the nanotubes 2 for a more complete examination of the sample. An AFM image of the sample can then be obtained according to standard AFM imaging techniques based upon the detected and mapped motion of the sample holder 21. The AFM system 25 can optionally work in contact, non-contact, or tapping mode, as desired. The disclosed system may provide additional benefits over more traditional AFM systems when operating in contact or tapping mode, as nanotubes are understood to be less fragile and more elastic than traditional AFM tips, such as those formed of silicon or silicon nitride. Accordingly, the disclosed system can be utilized with less down time due to probe damage and replacement as compared to more traditional systems.

In addition to AFM imaging capabilities, the system can also include NSOM imaging capabilities. For instance, as the interaction between the sample 8 and the plasmons can still induce a detectable change in the light intensity of the scattered evanescent waves from the prism, lens 7 and light intensity detector 26 can be utilized to construct an NSOM image as described above.

If desired, and as the interaction between the sample 8 and the nanotubes 2 can also induce a change in the light intensity reflected back from the 0/1 interface at 4', a light intensity detector 27 can be utilized to construct an NSOM image by mapping the reflected light 4'. This NSOM image will be the complement of an NSOM image constructed from the data at the light intensity detector 26 and can be obtained in addition to or as an alternative to such an image.

In this particular embodiment, rather than a single array of nanotubes, as illustrated in the embodiment of FIG. 2, groupings of nanotubes 2a, 2b, 2c can be mounted on the prism 11. For example, groupings of nanotubes can include groups of a single nanotube, as at 2c, as well as groups of multiple nanotubes, as at 2b and 2a. Location and density of the nanotubes grown on a substrate can be readily controlled through controlled deposition of catalyst on the substrate during a formation process, as discussed above. In addition, the prism 11 can be mounted on a mechanical stage that can be precisely located.

Such an embodiment can provide additional benefits to the disclosed system. For example, should a nanotube grouping become damaged, the prism can be simply translated to a second grouping through movement of the mechanical stage, and the system need not be shut down for probe replacement. In addition, multiple groupings of different sizes can be utilized to provide a wide range of information about the sample. In particular, data obtained with fewer nanotubes can provide increased image resolution, though the signal strength and/or image contrast will be decreased. However, the converse is also true, and data obtained with a large number of nanotubes can provide increased signal strength but lower resolution. For example, through utilization of a single nanotube, as at 2c, optical image resolution can be on the scale of the diameter of the nanotube, e.g., about 10 nm in the case of a MWNT, but the sample 8 would need to be relatively close to the end of the nanotube, within about 50 µm. Conversely, signal strength or image contrast can be enhanced by using a nanotube array of an increasing number of tubes, as at 2a and 2b, which would also allow greater distance between the nanotubes and the sample, for instance up to about 100 μm, but this will result in reduced image resolution. Accordingly, the disclosed system can provide a strong signal-to-noise ratio with the additional capability of obtaining information about a sample under a wide variety of examination conditions, e.g., extremely strong signal conditions as well as extremely high resolution conditions and any desired combination thereof, so as to provide a great deal of both topological and optical information concerning a sample of interest.

The systems of the present invention also provide an advantage over more traditional systems in that the nanotubes can relay an evanescent field over a large distance (e.g., on the order of micrometers), and as such the interaction between the sample and the evanescent field can be better isolated from the rest of the system. Accordingly, the presently disclosed systems need not suffer from shadowing effects common in more traditional systems due to the protrusion of a bulky fiber or a mechanical cantilever into the imaged region.

In addition, the disclosed system configuration avoids the use of a fiber probe for NSOM imaging and the costs associated with the chemical etching and/or mechanical tapering necessary for formation of such probes.

The present invention may be better understood with reference to the Example, below.

EXAMPLE

Figure 4:
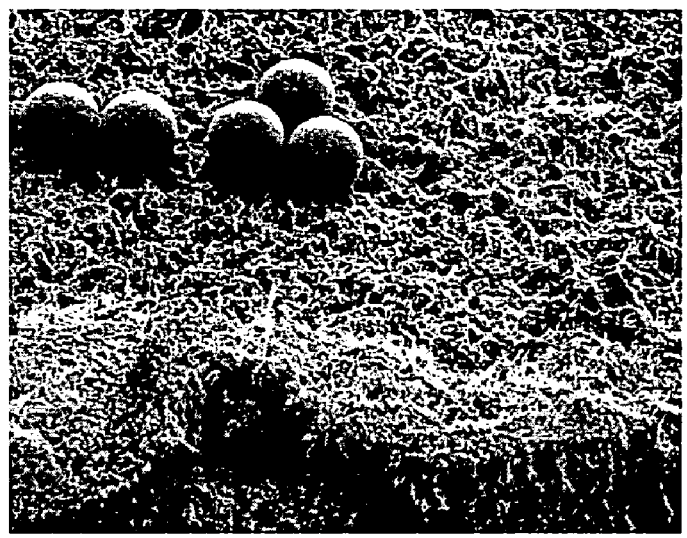
FIG. 4 is a scanning electron micrograph of a multi-walled carbon nanotube (MWNT) array as may be utilized according to one embodiment of the disclosed devices.

An experimental system as is illustrated in FIG. 2 was utilized. The system included a BK7 dove prism 11, a MWNT array 2 approximately 2 μm in thickness grown on a quartz slide (not shown) through the catalytic pyrolysis of a ferrocene-xylene mixture at 675° C. fed into a two-stage tubular quartz reactor, such as that illustrated in FIG. 1. A scanning electron microscopy (SEM) image, shown in FIG. 4, revealed that the aligned MWNTs grew perpendicular to the surface of the quartz substrate. The average number of layers of the graphite sheets for a single MWNT was approximately 20.

Fluorescent beads 8 (sky blue, φ=2 μm, available from Spherotech of Munich, Bavaria, Germany) were immobilized on the MWNT array 2. The absorption spectrum of the fluorescent beads 8 ranged from 500 nm up to approximately 800 nm. The beads were utilized to act as a probe for detecting plasmons coupled from the evanescent photons. A half waveplate 6 was used to change the polarization direction of the incident linearly-polarized laser beam 4 (incident angle of 81.1°, Nd:YAG 532 nm, 50 mW, CrystaLaser).

As shown in FIG. 2, light impinged the interface 3 between the quartz slide and the MWNT array 2 (0/1 interface) under the total-internal-reflection condition. An evanescent wave of the correct polarization and wavelength generated at the 0/1 interface 3 excited the plasmons in the MWNT array 2 which in turn produced plasmons on the upper surface of the MWNT array 2 at the 1/2 interface 5. Above the array 2, the enhanced evanescent field decayed exponentially away from the MWNT array 2, and excited the fluorescence of the sky blue beads 8 positioned within their proximity. The fluorescence from the beads was monitored using a CCD camera 26 (Roper Cascade 512B). An emitter 9 (Omega, 565ALP) inserted in front of the camera lens 7 served to remove stray light from the laser beam.

Figure 5:
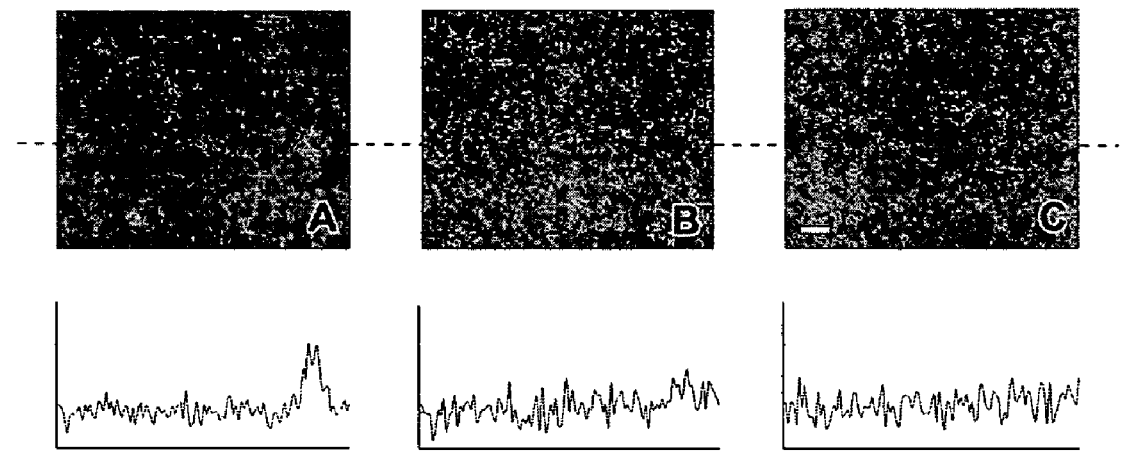
FIG. 5A-5C display images of fluorescent beads immobilized on a MWNT array and imaged via one embodiment of the disclosed invention utilizing impingement of p-polarized light (FIG. 5A), 5° off of p-polarized light (FIG. 5B), and s-polarized light (FIG. 5C), respectively.

Images were taken of the fluorescent beads 8 immobilized on the MWNT array 2 upon application of p-polarized, 5° off s-polarized, and s-polarized light respectively. Resulting images are shown in FIGS. 5A-5C, respectively. The corresponding intensity profiles along the dashed line are shown below each of these images. Except for the polarization direction, all three images were recorded under the same condition. In FIG. 5A, fluorescence from three beads was detected and a prominent peak corresponding to the bead on the right is displayed in the intensity profile. In contrast, the beads are faintly visible in FIG. 5B and invisible in FIG. 5C. Accordingly, no pronounced fluorescence peaks appeared in the intensity profiles for either image. This dependence of the fluorescence signal on the beam polarization confirmed that the fluorescence from beads was indeed excited by the plasmons bound to the MWNT surface, since plasmons are known to be generated only with p-polarized light. For s-polarized light, all the electric and magnetic components are continuous across the interface between the bead and the MWNT array according to Maxwell's boundary conditions. Therefore, no surface charge density will be induced for s-polarized light to form collectively oscillating plasmons.

In this experiment, the 2 μm thickness of the MWNT array ensured that no direct excitation of fluorescence was possible, since the penetration depth of the evanescent field is approximately 100 nm from the 0/1 interface 3. The observed experimental result may be interpreted as plasmons excited at the upper surface of the MWNT array being absorbed by the sky blue beads, which in turn emit light.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. An optical device comprising:
    a carbon nanotube, wherein surface plasmons exist on the carbon nanotube;
    a substrate, wherein the substrate allows the coupling of photons with the surface plasmons to give rise to surface plasmon polaritons;
    a light source, wherein the light source provides photons to a first end of the carbon nanotube to give rise to the surface plasmon polaritons, and photonic energy is radiated from the surface plasmon polaritons at a second end of the carbon nanotube; and
    a detector for detecting the photonic energy radiated from the surface plasmon polaritons.

2. The optical device of claim 1, further comprising a sample support, wherein photonic energy radiated from the surface plasmon polaritons contacts a sample located on the sample support.

3. The optical device of claim 1, wherein the carbon nanotube is a member of an array of carbon nanotubes.

4. The optical device of claim 3, wherein a surface of the array of carbon nanotubes is a sample support.

5. The optical device of claim 3, wherein the array of carbon nanotubes is a highly ordered array of carbon nanotubes.

6. The optical device of claim 1, wherein the detector is a position sensing point detector.

7. The optical device of claim 1, wherein the detector is a light intensity detector.

8. The optical device of claim 1, wherein the carbon nanotube is a multiwalled carbon nanotube.

9. The optical device of claim 1, wherein the substrate comprises a nonlinear optical material.

10. The optical device of claim 9, wherein the nonlinear optical material has a selectively variable index of refraction.

11. The optical device of claim 1, wherein the carbon nanotube is a doped carbon nanotube.

12. The optical device of claim 1, wherein the carbon nanotube is between about 1 micrometer and about 30 micrometers in length.

13. The optical device of claim 1, wherein the optical device is a plasmon waveguide.

14. The optical device of claim 1, wherein the optical device is an imaging device.

15. An optical device comprising:
a carbon nanotube, wherein surface plasmons exist on the carbon nanotube;
a substrate, wherein the substrate allows the coupling of photons with the surface plasmons to give rise to surface plasmon polaritons;
a light source, wherein the light source provides photons to a first end of the carbon nanotube to give rise to the surface plasmon polaritons, and photonic energy is radiated from the surface plasmon polaritons at a second end of the carbon nanotube;
a sample support, wherein photonic energy radiated from the surface plasmon polaritons contacts a sample located on the sample support;
a light intensity detector for detecting photonic energy radiated from the surface plasmon polaritons; and
a position sensing point detector for detecting photonic energy radiated from the surface plasmon polaritons.

16. The optical device of claim 15, wherein the carbon nanotube is one of a plurality of carbon nanotubes.

17. The optical device of claim 16, wherein the plurality of carbon nanotubes comprises a highly ordered array of carbon nanotubes.

18. The optical device of claim 15, wherein photonic energy detected by the light intensity detector is mapped to construct an optical image of the sample.

19. The optical device of claim 15, wherein photonic energy detected by the position sensing point detector is mapped to form a topological image of the sample.

20. A method for utilizing photonic energy comprising:
providing a carbon nanotube, wherein surface plasmons exist on the carbon nanotube;
at a first end of the carbon nanotube, coupling the surface plasmons with photons to generate surface plasmon polaritons;
at second end of the carbon nanotube, emitting photonic energy from the surface plasmon polaritons; and
detecting the photonic energy radiated from the surface plasmon polaritons.

21. The method according to claim 20, further comprising contacting a sample with the photonic energy radiated from the surface plasmon polaritons, wherein the step of detecting the photonic energy is carried out subsequent to contacting the sample with the photonic energy.

22. The method according to claim 21, further comprising forming an image of the sample.

23. The method according to claim 22, wherein the image is a near-field scanning optical microscopy image.

24. The method according to claim 22, wherein the image is an atomic force microscopy image.

25. The method according to claim 20, wherein the surface plasmon polaritons are transported from the first end of the carbon nanotube to the second end of the carbon nanotube over a distance greater than about 1 micrometer.

26. The method according to claim 20, wherein the photonic energy is detected with a light intensity detector.

27. The method according to claim 20, wherein the photonic energy is detected with a position sensing point detector.

28. The method according to claim 20, wherein the photonic energy is simultaneously detected with a light intensity detector and with a position sensing point detector.

* * * * *

UNITED STATES PATENT AND TRADEMARK OFFICE
CERTIFICATE OF CORRECTION

PATENT NO. : 7,456,972 B2  Page 1 of 1
APPLICATION NO. : 11/332840
DATED : November 25, 2008
INVENTOR(S) : Pu-Chun Ke et al.

It is certified that error appears in the above-identified patent and that said Letters Patent is hereby corrected as shown below:

In the specification

Column 1, lines 14 - 16 states,

"The United States Government may have rights in this invention pursuant to National Science Foundation Grant No. NIRT 0210559."

Please correct this paragraph to read as follows:

--This invention was made with government support under 210559 awarded by the National Science Foundation. The government has certain rights in the invention.--

Signed and Sealed this
Twenty-sixth Day of April, 2016

Michelle K. Lee
*Director of the United States Patent and Trademark Office*